(12) United States Patent
Balanev et al.

(10) Patent No.: US 8,444,664 B2
(45) Date of Patent: May 21, 2013

(54) MEDICAL ULTRASOUND INSTRUMENT WITH ARTICULATED JAWS

(75) Inventors: Andrey Balanev, Saint-Petersburg (RU); Georgy Martsinovskiy, Saint-Petersburg (RU); Igoris Misuchenko, Saint-Petersburg (RU); Alexey Ruin, Saint-Petersburg (RU); Vladimir Vasil'ev, Saint-Petersburg (RU)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/108,117

(22) Filed: May 16, 2011

(65) Prior Publication Data

US 2012/0296356 A1   Nov. 22, 2012

(51) Int. Cl.
*A61B 17/32* (2006.01)
(52) U.S. Cl.
USPC ............................. 606/169; 606/205; 606/52
(58) Field of Classification Search
USPC .................. 606/37, 39, 45, 51, 52, 169, 170, 606/171, 205, 206, 207, 208
See application file for complete search history.

(56) References Cited

U.S. PATENT DOCUMENTS

| | | |
|---|---|---|
| 3,469,211 A | 10/1967 | Shoh et al. |
| 4,277,710 A | 7/1981 | Harwood et al. |
| 4,587,958 A | 5/1986 | Noguchi et al. |
| 4,827,911 A | 5/1989 | Broadwin et al. |
| 4,922,902 A | 5/1990 | Wuchinich et al. |
| 4,965,532 A | 10/1990 | Sakurai |
| 4,973,876 A | 11/1990 | Roberts |
| 5,180,363 A | 1/1993 | Idemoto et al. |
| 5,216,338 A | 6/1993 | Wilson |
| 5,330,502 A | 7/1994 | Hassler et al. |
| 5,421,829 A | 6/1995 | Olichney et al. |
| 5,456,684 A | 10/1995 | Schmidt et al. |
| 5,532,539 A | 7/1996 | Hielscher |
| 5,562,682 A | 10/1996 | Oberlin et al. |
| 5,634,466 A | 6/1997 | Gruner |
| 5,637,947 A | 6/1997 | Kising et al. |

(Continued)

FOREIGN PATENT DOCUMENTS

| | | |
|---|---|---|
| AU | 200179486 B2 | 5/2002 |
| CA | 2 359 403 A1 | 4/2002 |

(Continued)

OTHER PUBLICATIONS

European Search Report for European Application No: 12168302.3 dated Aug. 10, 2012.

*Primary Examiner* — Ryan Severson
*Assistant Examiner* — Jonathan W Miles

(57) ABSTRACT

A forceps includes a housing, a shaft assembly, an end effector assembly, and a waveguide assembly. The housing has one or more transducers that generate a mechanical vibration in response to energy transmitted thereto from an energy source. The shaft assembly extends from the housing and includes one or more articulating and clamping members and a longitudinal axis defined therethrough. The end effector assembly is disposed at a distal end of the shaft assembly and includes a pair of opposing jaw members pivotable between approximated and unapproximated configurations in response to movement of the one or more clamping members. The articulating members articulate the jaw members relative to the longitudinal axis of the shaft assembly. The waveguide assembly is positioned within the shaft assembly and receives the mechanical vibration generated by the transducer. The waveguide assembly is positionable within one or both of the jaw members.

20 Claims, 8 Drawing Sheets

U.S. PATENT DOCUMENTS

| | | | |
|---|---|---|---|
| 5,649,957 A | 7/1997 | Levin | |
| 5,700,952 A | 12/1997 | Andersen | |
| 5,702,408 A | 12/1997 | Wales et al. | |
| 5,704,534 A | 1/1998 | Huitema et al. | |
| 5,797,537 A | 8/1998 | Oberlin et al. | |
| 5,816,476 A | 10/1998 | Buice et al. | |
| 5,817,119 A | 10/1998 | Klieman et al. | |
| 5,897,523 A | 4/1999 | Wright et al. | |
| 6,063,098 A | 5/2000 | Houser et al. | |
| 6,163,100 A | 12/2000 | Morizaki et al. | |
| 6,241,139 B1 | 6/2001 | Milliman et al. | |
| 6,320,298 B1 | 11/2001 | Kawabe | |
| 6,454,782 B1 | 9/2002 | Schwemberger et al. | |
| 6,480,796 B2 | 11/2002 | Wiener | |
| 6,569,109 B2 | 5/2003 | Sakurai et al. | |
| 6,588,277 B2 | 7/2003 | Giordano et al. | |
| 6,626,926 B2 | 9/2003 | Friedman et al. | |
| 6,652,547 B2 | 11/2003 | Rabiner et al. | |
| 6,663,641 B1 | 12/2003 | Kovac et al. | |
| 6,666,854 B1 | 12/2003 | Lange | |
| 6,678,621 B2 | 1/2004 | Wiener et al. | |
| 6,679,899 B2 | 1/2004 | Wiener et al. | |
| 6,752,815 B2 | 6/2004 | Beaupre | |
| 6,761,690 B2 | 7/2004 | Sakurai et al. | |
| 6,898,536 B2 | 5/2005 | Wiener et al. | |
| 6,984,919 B2 | 1/2006 | Iino et al. | |
| 7,179,271 B2 | 2/2007 | Friedman et al. | |
| 7,247,141 B2 | 7/2007 | Makin et al. | |
| 7,270,646 B2 | 9/2007 | Sakurai et al. | |
| 7,273,483 B2 | 9/2007 | Wiener et al. | |
| 7,475,801 B2 | 1/2009 | Johansen et al. | |
| 7,481,824 B2 | 1/2009 | Boudreaux et al. | |
| 7,482,888 B1 | 1/2009 | Kleveland | |
| 7,503,895 B2 | 3/2009 | Rabiner et al. | |
| 7,513,160 B2 | 4/2009 | Lynch et al. | |
| 7,514,844 B2 | 4/2009 | Unkrich | |
| 7,528,670 B2 | 5/2009 | Soh | |
| 7,566,334 B2 | 7/2009 | Christian et al. | |
| 7,614,878 B2 | 11/2009 | Paschke et al. | |
| 2002/0002380 A1* | 1/2002 | Bishop | 606/169 |
| 2005/0027311 A1 | 2/2005 | Wiener et al. | |
| 2005/0070800 A1 | 3/2005 | Takahashi | |
| 2006/0190031 A1* | 8/2006 | Wales et al. | 606/205 |
| 2008/0234711 A1 | 9/2008 | Houser et al. | |
| 2008/0277447 A1 | 11/2008 | Smith et al. | |
| 2008/0294191 A1 | 11/2008 | Lee | |
| 2008/0308607 A1 | 12/2008 | Timm et al. | |
| 2009/0036913 A1 | 2/2009 | Wiener et al. | |
| 2009/0036914 A1 | 2/2009 | Houser | |
| 2009/0065549 A1 | 3/2009 | Viola | |
| 2009/0069842 A1 | 3/2009 | Lee et al. | |
| 2009/0076534 A1 | 3/2009 | Shelton, IV et al. | |
| 2009/0118751 A1 | 5/2009 | Wiener et al. | |
| 2009/0131962 A2 | 5/2009 | Houser et al. | |
| 2009/0143797 A1 | 6/2009 | Smith et al. | |
| 2009/0143800 A1* | 6/2009 | Deville et al. | 606/169 |
| 2009/0187185 A1 | 7/2009 | Lyons et al. | |
| 2009/0198272 A1 | 8/2009 | Kerver et al. | |
| 2010/0030248 A1* | 2/2010 | Palmer et al. | 606/169 |

FOREIGN PATENT DOCUMENTS

| | | |
|---|---|---|
| EP | 0908155 | 4/1999 |
| EP | 1 199 046 B1 | 4/2002 |
| EP | 1 201 196 B1 | 3/2006 |
| EP | 2 000 106 A1 | 12/2008 |
| JP | 2000-237204 A | 9/2000 |
| WO | WO 02/062241 A1 | 8/2002 |

* cited by examiner

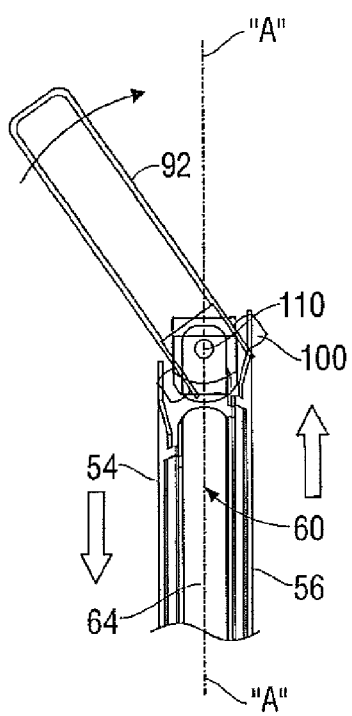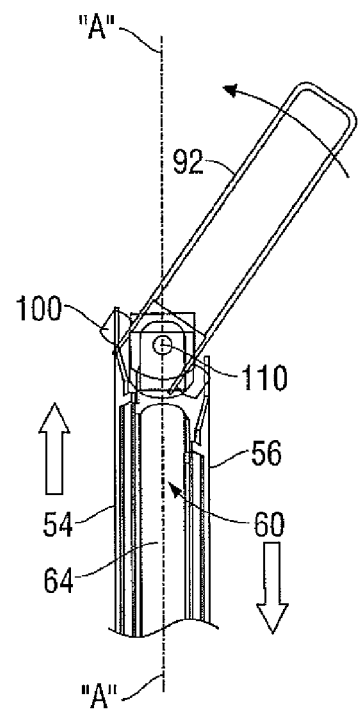
FIG. 12  FIG. 13

MEDICAL ULTRASOUND INSTRUMENT WITH ARTICULATED JAWS

BACKGROUND

1. Technical Field

The present disclosure relates to endoscopic surgical instruments. More particularly, the present disclosure relates to an endoscopic forceps that utilizes ultrasound to seal and cut tissue.

2. Background of the Related Art

As an alternative to open instruments for use with open surgical procedures, many modern surgeons use endoscopes and endoscopic electrosurgical apparatuses (e.g., endoscopic or laparoscopic forceps) for remotely accessing organs through smaller, puncture-like incisions. These instruments are particularly suited for use in minimally invasive procedures, such as endoscopic or laparoscopic procedures where patients tend to benefit from less scarring, less pain, and reduced healing time. Typically, the endoscopic forceps is inserted into the patient through one or more various types of cannulas or access ports (typically having an opening that ranges from about five millimeters to about fifteen millimeters) that has been made with a trocar; as can be appreciated, smaller cannulas are usually preferred.

Some endoscopic instruments may utilize ultrasound vibrations to effectuate certain medical procedures. In particular, ultrasonic instruments utilize mechanical vibration energy transmitted at ultrasonic frequencies to treat tissue. When transmitted at suitable energy levels, ultrasonic vibrations may be used to coagulate, cauterize, fuse, seal, cut, desiccate, and/or fulgurate tissue to effect hemostasis.

An endoscopic forceps that utilizes ultrasound and is configured for use with small cannulas (e.g., cannulas less than five millimeters) may present design challenges for a manufacturer of endoscopic instruments.

SUMMARY

Accordingly, the present disclosure is directed to a forceps including a housing, a shaft assembly, an end effector assembly, a trigger assembly, a rotating assembly, an articulator, and a waveguide assembly. The housing has one or more transducers. The one or more transducers are configured to generate a mechanical vibration in response to energy transmitted thereto from an energy source. The mechanical vibration may have an ultrasonic frequency. The forceps may include a battery that acts as the energy source. The battery may be a smart battery.

The shaft assembly extends from the housing and includes one or more articulating members and one or more clamping members. A longitudinal axis is defined through the shaft assembly. The end effector assembly is disposed at a distal end of the shaft assembly and includes a pair of opposing jaw members pivotable between approximated and unapproximated configurations in response to movement of the one or more clamping members. One or both of the pair of jaw members includes an engaging member that is operative associated with the clamping member such that movement of the clamping member pivots the engaging member such that the pair of opposing jaw members is positionable between the approximated and unapproximated configurations. The pair of opposing jaw members articulates relative to the shaft assembly about an axis transverse to the longitudinal axis of the shaft assembly. One or both of the pair of jaw members defines a channel therethrough.

The one or more articulating members are configured to articulate the pair of opposing jaw members relative to a longitudinal axis of the shaft assembly. Each articulating member is longitudinally translatable to move the pair of jaw members. In some embodiments, a first articulating member moves in a direction opposite a second articulating member to articulate the pair of jaws in a lateral direction. Each articulating member is operably coupled to one or both of the pair of jaw members by one or more ball bearings operably coupled to one or both of the pair of jaw members such that the one or more articulating members move along an outer surface of the one or more ball bearings as the pair of jaw members articulates. In some embodiments, two or more articulating members simultaneously move in the same longitudinal direction such that the end effector assembly longitudinally translates with respect to the waveguide assembly.

The waveguide assembly is positioned within the shaft assembly and is configured to receive the mechanical vibration generated by the transducer. The waveguide assembly is at least partially positionable within one or more of the opposing jaw members. The waveguide assembly includes a waveguide and an ultrasonic treatment member. The ultrasonic treatment member is configured to receive the mechanical vibration from the one or more transducers and transmit the mechanical vibration to treat tissue positioned between the pair of opposing jaw members. At least a portion of the ultrasonic treatment member is positionable within the channel defined by one or both of the pair of jaw members. When the ultrasonic treatment member is positioned within the channel, the end effector assembly is prevented from articulating. The waveguide assembly may be longitudinally translatable with respect to the end effector assembly.

The trigger assembly is operably coupled to the housing. The trigger assembly includes an activation trigger and a clamping trigger. The activation trigger is configured to facilitate the transmission of the energy from the energy source to the one or more transducers upon the actuation thereof. The clamping trigger is configured to move the one or more clamping members in order to move the pair of opposing jaw members between unapproximated and approximated configurations upon the actuation thereof.

The rotating assembly is operably coupled to the shaft assembly. The rotating assembly is configured to rotate the shaft assembly and the end effector assembly upon rotation thereof.

The articulator is operably coupled to the one or more articulating members. The one or more articulating members move in response to movement of articulator.

BRIEF DESCRIPTION OF THE DRAWINGS

The above and other aspects and features of the present disclosure will become more apparent in light of the following detailed description when taken in conjunction with the accompanying drawings in which:

FIGS. 12-13 are progressive, top views of the distal end of the ultrasound instrument of FIG. 4 illustrating the presently disclosed end effector assembly moving between articulated configurations.

DETAILED DESCRIPTION OF EMBODIMENTS

Figure 1:
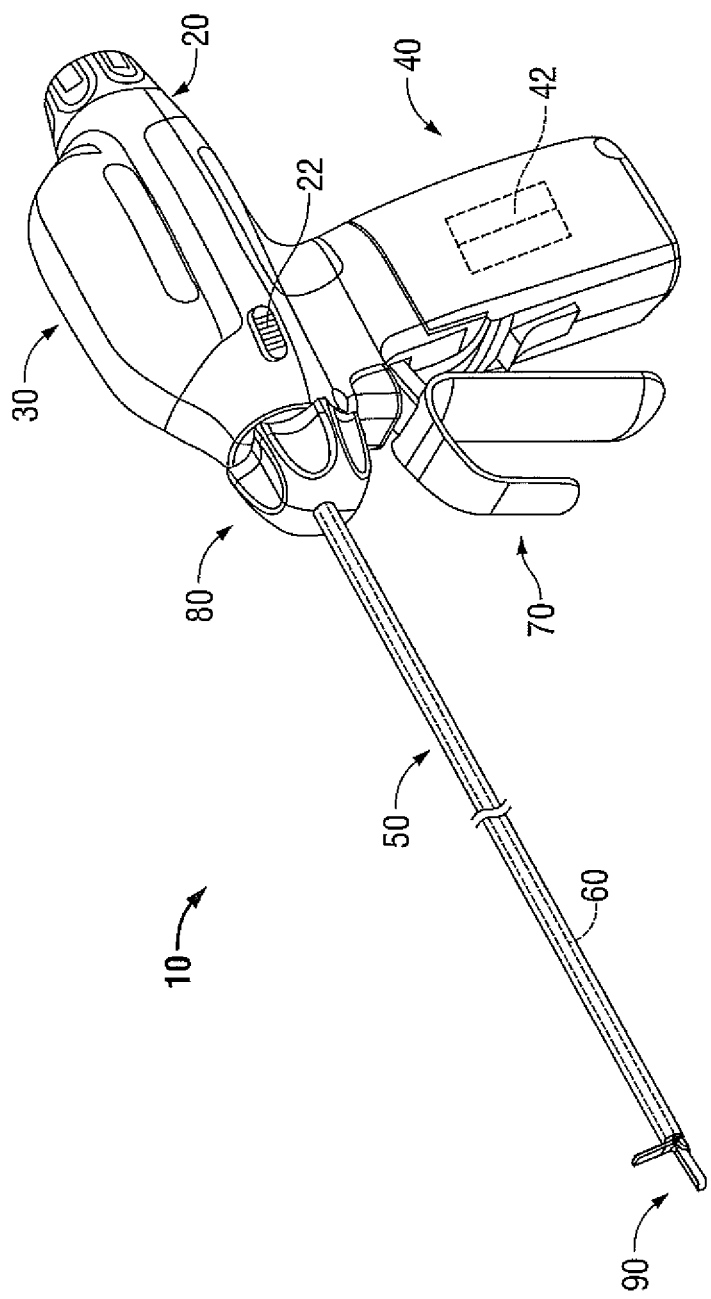
FIG. 1 shows a perspective view of one example of an ultrasonic instrument.

Detailed embodiments of the present disclosure are disclosed herein with reference to the accompanying drawings; however, the disclosed embodiments are merely examples of the disclosure, which may be embodied in various forms. As shown in the drawings and as described throughout the following description, and as is traditional when referring to relative positioning on an object during proper use, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Turning now to FIG. 1, an embodiment of an endoscopic forceps 10 is shown for use with various surgical procedures and generally includes a housing 20, a transducer assembly 30, an energy assembly 40, a shaft assembly 50, a waveguide assembly 60, a trigger assembly 70, a rotating assembly 80, and an end effector assembly 90 that mutually cooperate to grasp, seal, and divide tubular vessels and vascular tissue.

Figure 2:
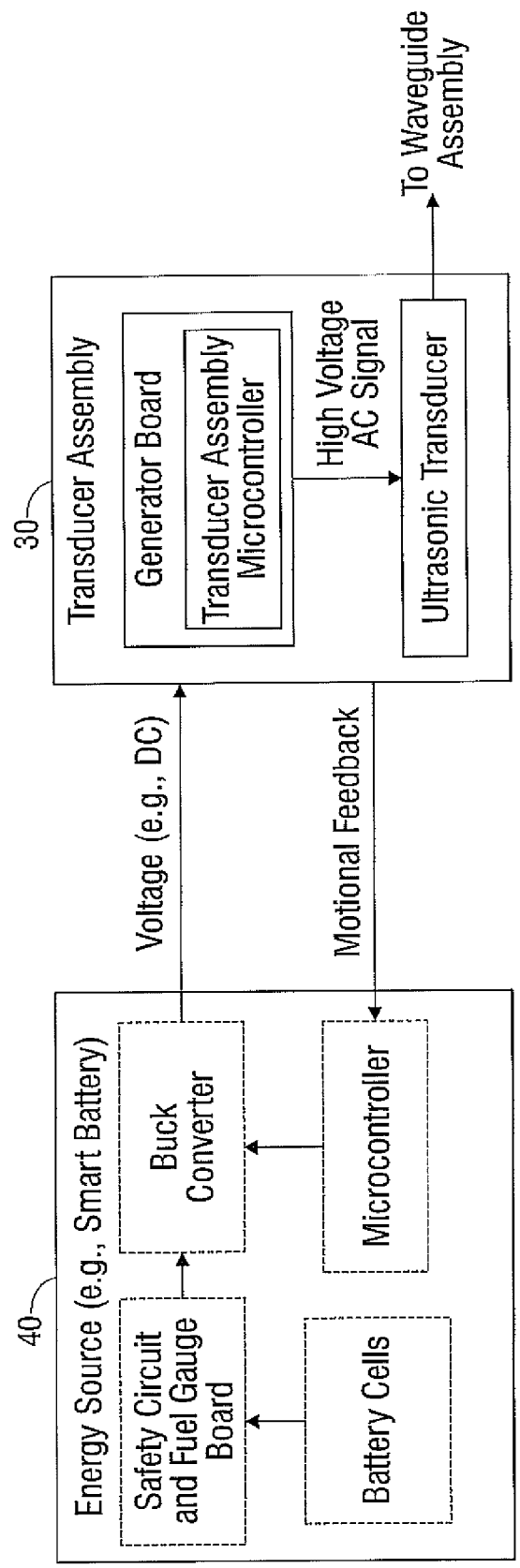
FIG. 2 is a block diagram depicting the interaction between an energy source and a transducer assembly of the ultrasonic instrument of FIG. 1.

Forceps 10 is powered by the energy assembly 40 when the energy assembly 40 is operably connected to the forceps 10. The energy assembly 40 may include one or more batteries 42 and/or one or more electrosurgical cables (not shown) to transfer energy, e.g. voltage from DC and/or AC signals, to the forceps 10. The forceps 10 may include a smart battery that controls the charge and discharge of its battery cells and communicates with the transducer assembly 30 as illustrated in FIG. 2. For a more detailed description of such an instrument, reference is made to commonly-owned U.S. application Ser. No. 12/269,544 filed on Nov. 12, 2009.

In embodiments with one or more electrosurgical cables, the forceps 10 is connectable to an external source of electrosurgical energy, e.g., an electrosurgical generator (not shown). One such source of electrosurgical energy is described in commonly-owned U.S. Pat. No. 6,033,399 entitled "ELECTROSURGICAL GENERATOR WITH ADAPTIVE POWER CONTROL."

Figure 3:
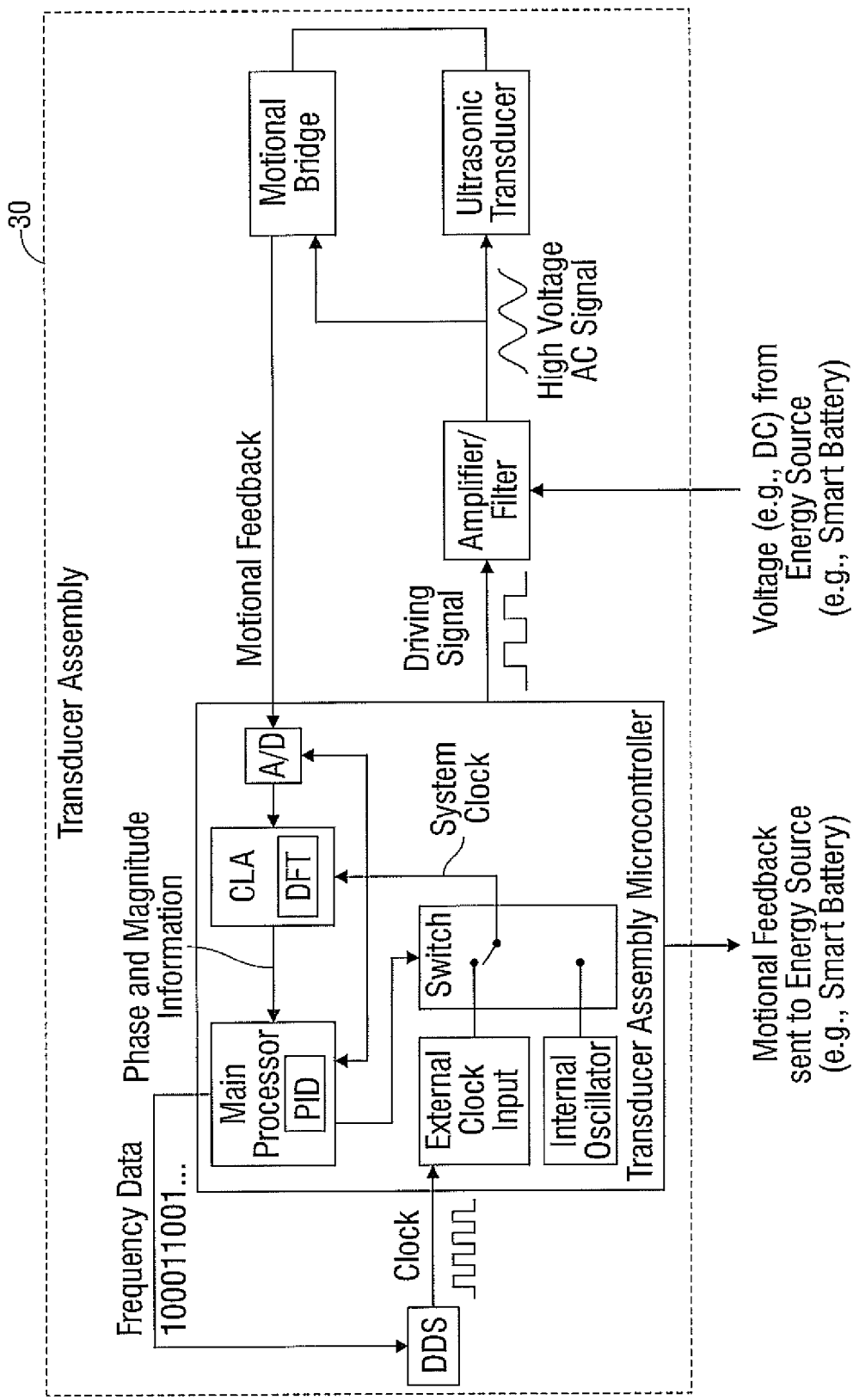
FIG. 3 is a block diagram depicting the transducer assembly of FIG. 2.
Figure 4:
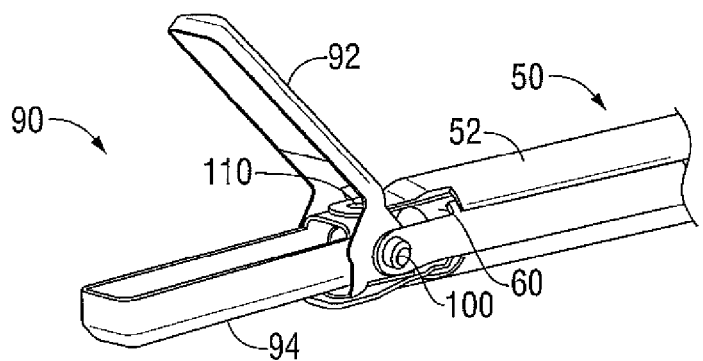
FIG. 4 is a right, perspective view of a distal end of one embodiment of an ultrasonic instrument in accordance with the present disclosure.

The transducer assembly 30 includes one or more ultrasonic transducers (not shown) operably coupled to the housing 20. Each transducer, which may be positioned within the housing 20, converts the energy transmitted thereto from the energy assembly 40 into high frequency mechanical motion, e.g., ultrasonic vibration. As such, the frequency of the ultrasonic vibration in the one or more transducers is controlled by the frequency of the energy signal, e.g., high voltage AC signal, applied to the one or more transducers. As depicted in FIG. 3, this frequency control may be accomplished by a phase-lock loop in the transducer assembly 30.

Figure 5:
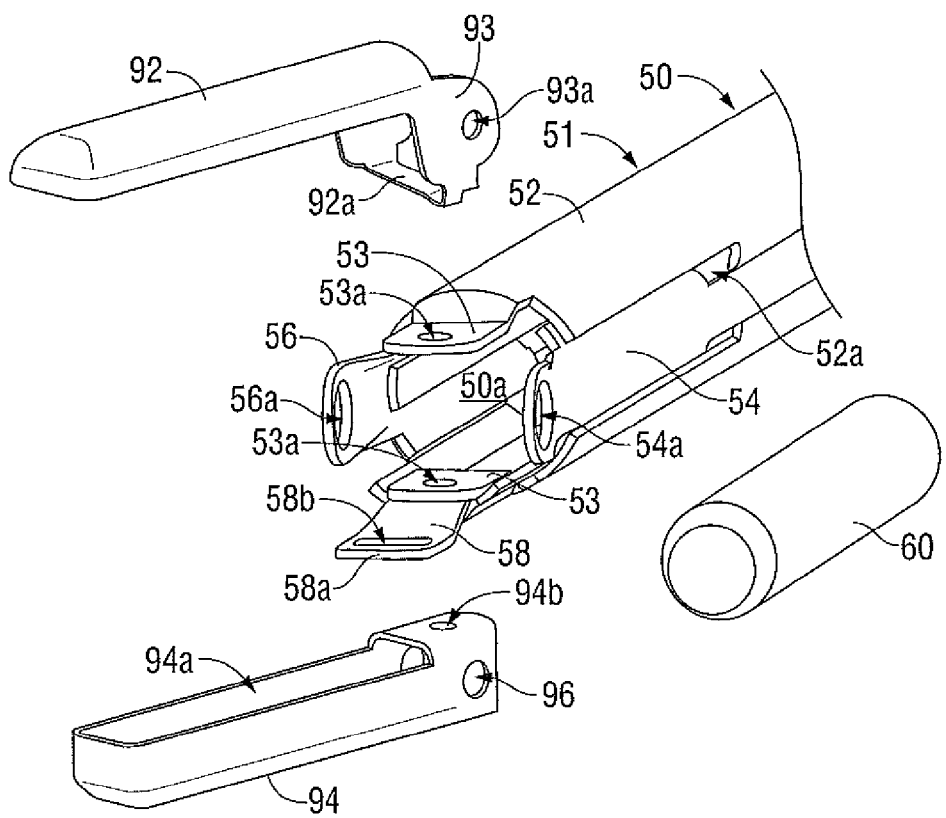
FIG. 5 is a right, perspective view, with parts separated, of the distal end of the ultrasound instrument of FIG. 4.
Figure 6:
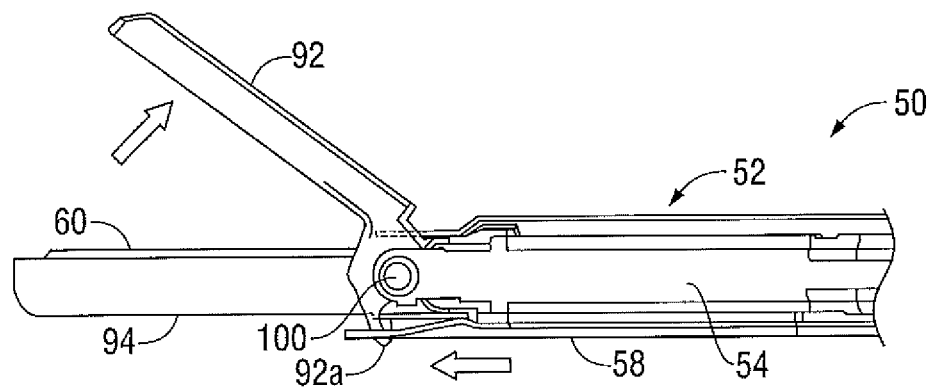
FIGS. 6 and 7 are right, side progressive views of the distal end of the ultrasound instrument of FIG. 4 with jaws of the presently disclosed end effector assembly thereof being shown positioned between approximated and unapproximated configurations.
Figure 7:
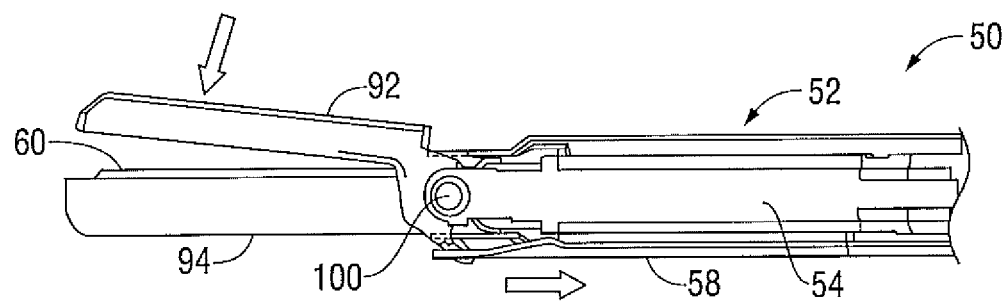

With reference to FIGS. 4-7, the shaft assembly 50, which may be at least partially disposable, extends from the housing 20 and defines a central lumen 50a therethrough (see FIG. 5). The central lumen 50a receives at least a portion of the waveguide assembly 60 therein. As best depicted in FIG. 5, the shaft assembly 50 includes a shaft 51, first and second articulating members 54, 56 and a clamping member 58. First and second articulating members 54, 56 and clamping member 58 are movably positioned along shaft 51. Shaft 51 includes an elongated body 52 having opposed distal support members 53 extending therefrom. The support members 53 are spaced apart and each support member 53 defines an opening 53a therethrough for engaging a pivot pin 110. In particular, elongated body 52 defines channels 52a thereal ong within which each of the first and second articulating members 54, 56 and the clamping member 58 are movably positioned. More specifically, the first and second articulating members 54, 56 are positioned along the shaft 51 on opposed sides of lateral surfaces of the shaft 51 so that first and second articulating members 54, 56 are longitudinally translatable along the opposed sides of the elongated body 52 of the shaft 51. Clamping member 58 is disposed along the bottom surface of the shaft 51 transverse to the first and second articulating members 54, 56. Accordingly, the clamping member 58 translates longitudinally along the shaft 51 transverse to the first and second articulating members 54, 56.

With continued reference to FIG. 5, clamping member 58 includes a distal driving member 58a extending therefrom. Distal driving member 58a defines an aperture 58b therethrough. As described in greater detail below, the proximal end of the clamping member 58 is operably coupled to the trigger assembly 70 for longitudinally translating the clamping member 58 relative to the shaft 51 of the shaft assembly 50 upon the actuation of the trigger assembly 70.

The distal ends of the first and second articulating members 54, 56 are operably coupled to the end effector assembly 90 and define ball slots 54a, 56a, respectively therethrough. Since the first and second articulating members 54, 56 are operably coupled to the end effector assembly 90, the first and second articulating members 54, 56 articulate the end effector assembly 90 relative to a longitudinal axis "A-A" (see FIGS. 12-13) defined through the shaft assembly 50 and/or translate the end effector assembly 90 along the longitudinal axis "A-A" of the shaft assembly 50.

Figure 10:
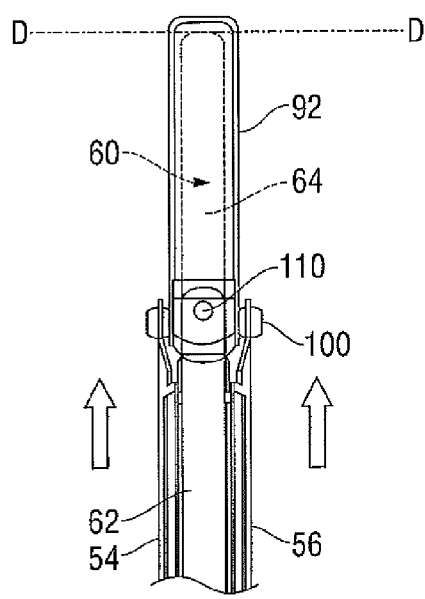
FIGS. 10-11 are progressive, top views of the distal end of the ultrasound instrument of FIG. 4 illustrating the positioning of the presently disclosed end effector assembly relative to the presently disclosed waveguide assembly, the presently disclosed end effector assembly being shown in an unarticulated configuration.
Figure 11:
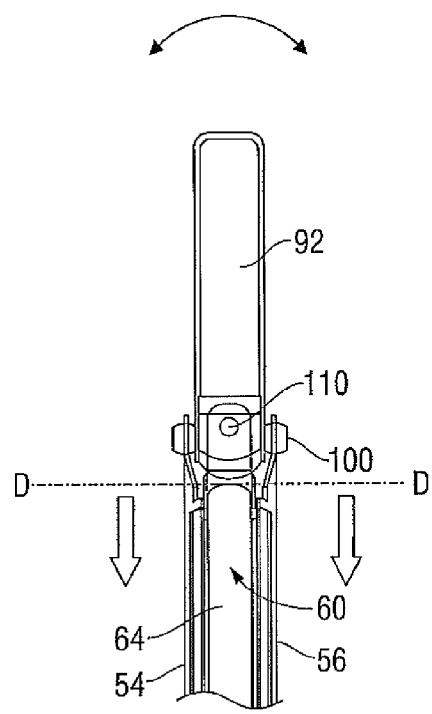

Referring again to FIG. 1, an articulator 22 (e.g., a knob, switch, or any other suitable mechanical control known in the art) mounts to the housing 20 and is operably coupled to the proximal end of the first and second articulating members 54, 56 such that the first and second articulating members 54, 56 move longitudinally in response to axial and/or rotational movement of articulator 22. In this regard, each of articulating members 54, 56 is longitudinally translatable by the articulator 22 to articulate and/or translate the end effector assembly 90. As shown in FIGS. 12-13, the first articulating member 54 moves in a direction opposite the second articulating member 56 to articulate the end effector assembly 90 in a lateral direction. Accordingly, the end effector assembly 90 can be configured to articulate relative to the shaft assembly 50 about an axis transverse to the longitudinal axis "A-A" of the shaft assembly 50. Further, the first and second articulating members 54, 56 can be configured to simultaneously extend and/or retract along the longitudinal axis "A-A" of the shaft assembly 50 to move the end effector assembly 90 proximally and/or distally relatively to the shaft assembly 50. As depicted in FIGS. 10-11, both articulating members 54, 56 simultaneously move in the same longitudinal direction such that the end effector assembly 90 longitudinally translates with respect to the waveguide assembly 60 to a distal position beyond a line (shown as line "D-D") at the tip of the waveguide assembly 60 in order to facilitate articulation of the end effector assembly 90 about the shaft and waveguide assemblies 50, 60.

Referring again to FIGS. 5-7, the end effector assembly 90, which may be at least partially disposable, includes a pair of opposing jaw members 92, 94. The first jaw member 92 includes a pivot arm 92a. The pivot arm 92a is engageable with the aperture 58b defined within the distal driving member 58a of clamping member 58 such that movement of the clamping member 58 pivots the first jaw member 92 relative to the second jaw member 94, positioning jaws 92, 94 between approximated and unapproximated configurations.

First Jaw member 92 includes a pivot flange 93 on the proximal end thereof. The pivot flange 93 defines a ball slot 93a on each side thereof so that a pair of ball bearings 100 can be coupled to each respective ball slot 93a. The ball bearings 100 will be described in greater detail below. Pivot flange 93 includes a pivot arm 122 that is engagable with the distal driving member 58a of the clamping member 58 to move the first jaw member 92 relative to the second jaw member 94. More particularly, the pivot arm 122 is positionable within aperture 58b of the distal driving member 58a so that the first jaw member 92 pivots about an axis transverse to the longitudinal axis "A-A" of the shaft assembly 50, rotating the first jaw member 92 away from the second jaw member 94. When the clamping member 58 is positioned in a distal-most position, the first jaw member 92 is in the unapproximated configuration (open) relative to the second jaw member 94. When the clamping member 58 is in the proximal-most position, the first jaw member 92 is in the approximated configuration (closed) relative to the second jaw member 94.

Second jaw member 94 defines a channel 94a therethrough. The second jaw member 94 also defines a pin slot 94b therethrough and ball slots 96 on opposed sides of the proximal end thereof. Ball slots 96 are configured to engage ball bearings 100 therein, which will be described in greater detail below. Pivot slot 94b aligns with opening 53a of support member 53 of shaft 51 to receive pivot pin 110 therethrough to further facilitate the articulation of end effector assembly 90 relative to shaft assembly 50. In this regard, the end effector assembly 90 is enabled to pivot about an axis transverse to the longitudinal axis "A-A" of the shaft assembly 50.

Jaw members 92, 94 may be formed from any suitable material, for example without limitation, metallic material such as aluminum and alloys thereof, plated brass, stainless steel, stainless steel alloys, beryllium copper, etc. In other embodiments, one or both jaw members 92 and 94 may be formed from material having malleable or flexible properties or, alternatively, one or both of jaw members 92 and 94 may be formed from a material having inflexible properties.

The ball bearings 100 are configured to engage the articulating members 54, 56 of the shaft assembly 50 and ball slots 96 defined in the second jaw to allow the end effector assembly 90 to articulate relative to the shaft assembly 50. In this manner, the articulating members 54, 56 move along an outer surface of ball bearings 100, facilitating the articulation of the end effector assembly 90.

Figure 8:
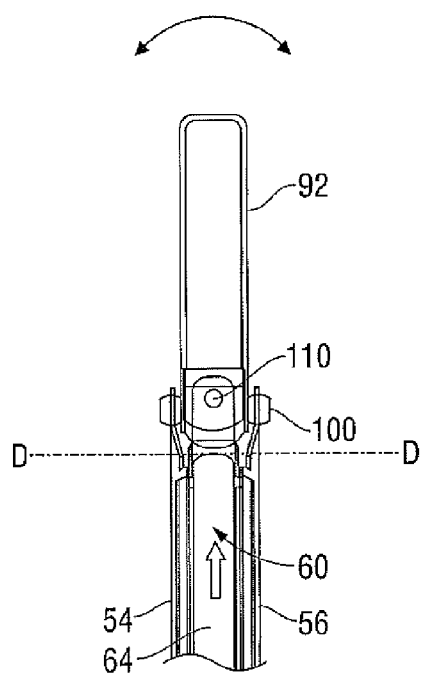
FIGS. 8-9 are progressive, top views of the distal end of the ultrasound instrument of FIG. 4 illustrating the positioning of the presently disclosed waveguide assembly thereof relative to the presently disclosed end effector assembly thereof, the presently disclosed end effector assembly being shown in an unarticulated configuration.
Figure 9:
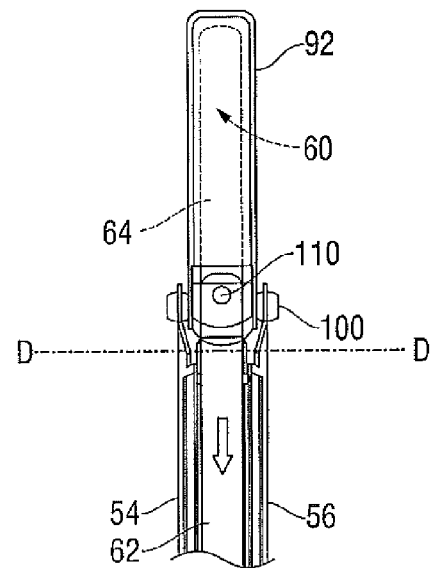

As best depicted in FIGS. 8-9, the waveguide assembly 60 is positioned within the shaft assembly 50 and is configured to receive and transmit the ultrasonic mechanical vibration generated by the one or more transducers. The waveguide assembly 60 includes a waveguide 62 and an ultrasonic treatment member 64 operably coupled to the distal end of the waveguide 62. The waveguide assembly 60 is at least partially positionable within one or both jaw members 92, 94 of the end effector assembly 90. More particularly, at least a portion of the ultrasonic treatment member 64 is positionable within the channel 94a defined by jaw member 94 of the end effector assembly 90. With reference to FIG. 9, when the ultrasonic treatment member 64 is positioned within the channel 94a beyond a line (shown as line "D-D") proximal of the end effector assembly 90, the end effector assembly 90 is prevented from articulating. However, when the ultrasonic treatment member 64 is positioned proximally behind the line (shown in FIG. 8 as line "D-D" at the tip of the waveguide assembly 60), articulation of the end effector assembly 90 about the shaft and waveguide assemblies 50, 60 is facilitated. In some embodiments, the ultrasonic treatment member 64 is integrally formed with the distal end of the waveguide 62. In some embodiments, the ultrasonic treatment member 64 may be movably coupled to the distal end of the waveguide 62. The ultrasonic treatment member 64 is configured to receive the mechanical vibration from the one or more transducers and transmit the mechanical vibration to treat tissue positioned within end effector assembly 90. The waveguide assembly 60 may be longitudinally translatable with respect to the end effector assembly 90.

The rotating assembly 80 is operatively connected to the housing 20 and is rotatable in either direction about the longitudinal axis of the shaft assembly 50 to rotate the shaft assembly 50 and the end effector assembly 90 about the longitudinal axis of the shaft assembly 50. This enables the user to position and re-position the forceps 10 prior to activation and sealing. The rotating assembly 80 is operably coupled to the shaft assembly 50. A more detailed description of rotating assembly 80 is described in U.S. Pat. No. 7,101, 371, entitled "VESSEL SEALER AND DIVIDER" by Dycus et al.

The trigger assembly 70 includes an activation trigger 72 for activating energy from the energy assembly 40 and a clamping trigger 74 for operating the end effector assembly 90. The trigger assembly 70 is operably coupled to the housing 20. The activation trigger 72 is configured to facilitate the transmission of the energy from the energy source to the one or more transducers upon the actuation thereof. The clamping trigger 74 is configured to move the clamping member 58 in order to move the opposing jaw members 92, 94 between unapproximated and approximated configurations upon the actuation of the clamping trigger 74. In this manner, the clamping trigger 74 of the trigger assembly 70 is operatively connected to the shaft assembly 50 to impart movement to first and second jaw members 92, 94 from an unapproximated (open) position, where the jaw members 92, 94 are in spaced relation relative to one another, to a clamping or approximated (closed) position, where the jaw members 92, 94 cooperate to grasp tissue therebetween.

In use, when the activation trigger 72 is actuated, the energy assembly 40 applies energy, e.g., the high voltage AC signal, to the transducer assembly 30. As discussed above, the energy is then converted by the transducer assembly 30 and transmitted from the transducer assembly 30 along the waveguide assembly 60 to the end effector assembly 90 in order to treat tissue grasped between the first and second jaws 92, 94 with ultrasonic vibrations.

With this purpose in mind, forceps 10 may include any suitable number of electrical connections, configurations, and/or components (e.g., resistors, capacitors, inductors, rheostats, etc.), mechanical connections, configurations, and/or components (e.g., gears, links, springs, members, etc.), and/or electro-mechanical connections, configurations, and/or components such that forceps 10 may function as intended.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   a housing having at least one transducer, the at least one transducer configured to generate a mechanical vibration in response to energy transmitted thereto from an energy source;
   a shaft assembly extending from the housing, the shaft assembly including at least one articulating member and at least one clamping member and a longitudinal axis defined therethrough;
   an end effector assembly disposed at a distal end of the shaft assembly and including a pair of opposing jaw members pivotable between approximated and unapproximated configurations in response to movement of the at least one clamping member, the at least one articulating member being configured to articulate the pair of opposing jaw members relative to the longitudinal axis of the shaft assembly; and
   a waveguide assembly positioned within the shaft assembly and configured to receive the mechanical vibration generated by the transducer, the waveguide assembly being at least partially positionable within at least one of the opposing jaw members;
   wherein the end effector is longitudinally translatable between a proximal position and a distal position with respect to the shaft assembly and the waveguide assembly to allow the end effector assembly to articulate relative to the shaft and the waveguide assembly when the end effector assembly is disposed in the distal position.

2. The forceps according to claim 1, wherein the pair of opposing jaw members articulates relative to the shaft assembly about an axis transverse to the longitudinal axis of the shaft assembly.

3. The forceps according to claim 1, wherein the shaft assembly includes at least two articulating members, each articulating member being longitudinally translatable to move the pair of jaw members.

4. The forceps according to claim 3, wherein a first articulating member moves in a direction opposite a second articulating member to articulate the pair of jaw members in a lateral direction.

5. The forceps according to claim 3, wherein the at least two articulating members simultaneously move in the same longitudinal direction such that the end effector assembly longitudinally translates with respect to the waveguide assembly.

6. The forceps according to claim 1, wherein each articulating member is operably coupled to at least one of the pair of jaw members by at least one ball bearing operably coupled to at least one of the pair of jaw members such that the at least one articulating member moves along an outer surface of the at least one ball bearing as the pair of jaw members articulates.

7. The forceps according to claim 1, wherein the waveguide assembly is longitudinally translatable with respect to the end effector assembly.

8. The forceps according to claim 1, wherein the waveguide assembly includes a waveguide and an ultrasonic treatment member, the ultrasonic treatment member configured to receive the mechanical vibration from the at least one transducer and transmit the mechanical vibration to treat tissue positioned between the pair of opposing jaw members.

9. The forceps according to claim 8, wherein at least one of the pair of jaw members defines a channel therethrough, wherein at least a portion of the ultrasonic treatment member is positionable within the channel.

10. The forceps according to claim 9, wherein when the ultrasonic treatment member is positioned within the channel defined by at least one of the pair of jaw, the end effector assembly is prevented from articulating.

11. The forceps according to claim 1, wherein at least one of the pair of jaw members includes an engaging member operatively associated with the clamping member such that movement of the clamping member pivots the engaging member such that the pair of opposing jaw members is positionable between the approximated and unapproximated configurations.

12. The forceps according to claim 1, wherein the mechanical vibration has an ultrasonic frequency.

13. The forceps according to claim 1, wherein the forceps includes a battery that acts as the energy source.

14. The forceps according to claim 13, wherein the battery is a smart battery.

15. The forceps according to claim 1, further comprising a trigger assembly operably coupled to the housing, the trigger assembly including an activation trigger and a clamping trigger, the activation trigger configured to facilitate the transmission of the energy from the energy source to the at least one transducer upon the actuation thereof, the clamping trigger configured to move the at least one clamping member in order to move the pair of opposing jaw members between unapproximated and approximated configurations upon the actuation thereof.

16. The forceps according to claim 1, further comprising a rotating assembly operably coupled to the shaft assembly, the rotating assembly configured to rotate the shaft assembly and the end effector assembly upon rotation thereof.

17. The forceps according to claim 1, further comprising an articulator operably coupled to the at least one articulating member, the at least one articulating member moving in response to movement of the articulator.

18. A forceps, comprising:
   a housing having at least one transducer, the at least one transducer configured to generate a mechanical vibration in response to energy transmitted thereto from an energy source;
   a shaft assembly extending from the housing, the shaft assembly defining a longitudinal axis and including at least one articulating member and at least one clamping member;
   a waveguide assembly positioned within the shaft assembly and being configured to receive the mechanical vibration generated by the transducer; and an end effector assembly disposed at a distal end of the shaft assembly and including a pair of opposing jaw members pivotable between approximated and unapproximated configurations in response to movement of the at least one clamping member, the at least one articulating member being configured to articulate the pair of opposing jaw members relative to the longitudinal axis of the shaft assembly, the end effector assembly being longitudinally translatable between a proximal position and a distal position with respect to the shaft assembly and the waveguide assembly to allow the end effector assembly to articulate relative to the shaft and the waveguide assembly when the end effector assembly is disposed in the distal position;

wherein the waveguide assembly is at least partially positionable within at least one of the opposing jaw members.

19. The forceps according to claim 18, wherein the at least one articulating member articulates the pair of opposing jaw members laterally relative to the longitudinal axis of the shaft assembly.

20. The forceps according to claim 18, wherein when the end effector assembly is in the proximal position, the end effector assembly is prevented from articulating.

* * * * *